US009482622B2

United States Patent
Sato et al.

(10) Patent No.: US 9,482,622 B2
(45) Date of Patent: Nov. 1, 2016

(54) METHODS AND APPARATUS FOR SURFACE CLASSIFICATION

(71) Applicants: Munehiko Sato, Cambridge, MA (US); Ramesh Raskar, Cambridge, MA (US); Boxin Shi, Singapore (SG); Alex Olwal, Stockholm (SE)

(72) Inventors: Munehiko Sato, Cambridge, MA (US); Ramesh Raskar, Cambridge, MA (US); Boxin Shi, Singapore (SG); Alex Olwal, Stockholm (SE)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/677,898

(22) Filed: Apr. 2, 2015

(65) Prior Publication Data

US 2015/0330905 A1 Nov. 19, 2015

Related U.S. Application Data

(60) Provisional application No. 61/994,749, filed on May 16, 2014.

(51) Int. Cl.

| | |
|---|---|
| G01N 21/00 | (2006.01) |
| G01N 21/84 | (2006.01) |
| G01N 21/25 | (2006.01) |
| G01N 21/47 | (2006.01) |
| G01N 21/31 | (2006.01) |

(52) U.S. Cl.
CPC ............ *G01N 21/84* (2013.01); *G01N 21/251* (2013.01); *G01N 21/255* (2013.01); *G01N 21/474* (2013.01); *G01N 2021/3155* (2013.01); *G01N 2021/3181* (2013.01); *G01N 2021/479* (2013.01); *G01N 2021/8444* (2013.01); *G01N 2201/062* (2013.01); *G01N 2201/0612* (2013.01); *G01N 2201/0627* (2013.01); *G01N 2201/06113* (2013.01); *G01N 2201/12* (2013.01)

(58) Field of Classification Search
CPC .............. G01J 3/02; G01J 3/513; G01J 3/51; G01N 15/1459; G01N 21/65
USPC ......................................................... 356/73
See application file for complete search history.

(56) References Cited

U.S. PATENT DOCUMENTS

| | | | |
|---|---|---|---|
| 6,327,374 B1 * | 12/2001 | Piironen | G01B 11/303 382/108 |
| 7,248,359 B2 | 7/2007 | Boege | |
| 7,460,696 B2 | 12/2008 | Rowe | |

(Continued)

OTHER PUBLICATIONS

Moy, D., Apr. 26, 2011, Optical mouse technology: Here to stay, still evolving. Accessed on Jun. 3, 2015 at http://www.electronicproducts.com/Sensors_and_Transducers/Image_Sensors_and_Optical_Detectors/Optical_mouse_technology_Here_to_stay_still_evolving.aspx.

(Continued)

*Primary Examiner* — Tarifur Chowdhury
*Assistant Examiner* — Md M Rahman
(74) *Attorney, Agent, or Firm* — Stephen R. Otis

(57) ABSTRACT

In illustrative implementations of this invention, light sources illuminate a surface with multi-spectral, multi-directional illumination that varies in direction, wavelength, coherence and collimation. One or more cameras capture images of the surface while the surface is illuminated under different lighting conditions. One or more computers take, as input, data indicative of or derived from the images, and determine a classification of the surface. Based on the computed classification, the computers output signals to control an I/O device, such that content displayed by the I/O device depends, at least in part, on the computed classification. In illustrative implementations, this invention accurately classifies a wide range of surfaces, including transparent surfaces, specular surfaces, and surfaces with few features.

12 Claims, 13 Drawing Sheets

(56) References Cited

U.S. PATENT DOCUMENTS

| | | | | |
|---|---|---|---|---|
| 2002/0008055 | A1* | 1/2002 | Campbell | B07C 5/3422 209/577 |
| 2002/0111546 | A1* | 8/2002 | Cook | A61B 5/14535 600/322 |
| 2010/0135454 | A1* | 6/2010 | Noo | G06T 11/006 378/9 |
| 2013/0128042 | A1* | 5/2013 | Bridge | H04N 5/232 348/143 |
| 2013/0303870 | A1* | 11/2013 | Satish | A61B 5/14535 600/371 |
| 2014/0331173 | A1* | 11/2014 | Minekawa | G06F 9/4443 715/803 |

OTHER PUBLICATIONS

Avago Technologies, Aug. 8, 2011, ADNS-9500 LaserStream Gaming Sensor Data Sheet. Accessed on Jun. 3, 2015 at http://media.digikey.com/pdf/Data%20Sheets/Avago%20PDFs/ADNS-9500.pdf.

Avago Technologies, Aug. 16, 2011, ADNS-6190-002 LaserStream Gaming Round Lens Data Sheet. Accessed on Jun. 3, 2015 at http://www.mouser.com/ds/2/38/V02-1725EN-75622.pdf.

Harrison, C., et al., 2008, Lightweight material detection for placement-aware mobile computing. Proceedings of the 21st annual ACM symposium on User interface software and technology, UIST '08, pp. 279-282, ACM New York, NY, USA, 2008.

Liu, C., et al., 2013, Discriminative Illumination: Per-Pixel Classification of Raw Materials Based on Optimal Projections of Spectral BRDF. IEEE Transactions on Pattern Analysis and Machine Intelligence, vol. 36, issue 1, pp. 86-98, published online Jun. 10, 2013.

Olwal, A., et al., 2012, SpeckleEye: gestural interaction for embedded electronics in ubiquitous computing. CHI Extended Abstracts, p. 2237-2242. ACM, (2012).

Shih, Y., et al., 2012, Laser Speckle Photography for Surface Tampering Detection. IEEE Conference on Computer Vision and Pattern Recognition (CVPR), 2012, pp. 33-40.

* cited by examiner

INCOHERENT LIGHT SOURCES ILLUMINATE A SURFACE WHILE ONE OR MORE CAMERAS CAPTURE IMAGES OF THE SURFACE, SUCH THAT:

FOR EACH OF ONE OR MORE TYPES OF INCOHERENT LIGHT SOURCES, RESPECTIVELY (EACH TYPE OF INCOHERENT LIGHT SOURCE BEING CHARACTERIZED BY SPECTRAL INTENSITY), FOR EACH LIGHT SOURCE IN THAT TYPE OF INCOHERENT LIGHT SOURCE (AND THUS FOR EACH POSITION OF THAT TYPE OF INCOHERENT LIGHT SOURCE) THE LIGHT SOURCE ILLUMINATES THE SURFACE WHILE THE ONE OR MORE CAMERAS CAPTURE AN IMAGE OR IMAGES OF THE SURFACE

FOR EACH OF THE ONE OR MORE TYPES OF INCOHERENT LIGHT SOURCES, RESPECTIVELY, ALL OF THE LIGHT SOURCES IN THAT TYPE OF INCOHERENT LIGHT SOURCE (AND THUS ALL OF THE POSITIONS OF THAT TYPE OF INCOHERENT LIGHT SOURCE) ILLUMINATE THE SURFACE SIMULTANEOUSLY WHILE THE ONE OR MORE CAMERAS CAPTURE AN IMAGE OR IMAGES OF THE SURFACE

501

ONE OR MORE COHERENT LIGHT SOURCES ILLUMINATE THE SURFACE WHILE ONE OR MORE CAMERAS CAPTURE IMAGES OF THE SURFACE, SUCH THAT:

FOR EACH OF ONE OR MORE TYPES OF COHERENT LIGHT SOURCES, RESPECTIVELY (EACH TYPE OF COHERENT LIGHT SOURCE BEING CHARACTERIZED BY SPECTRAL INTENSITY), FOR EACH LIGHT SOURCE IN THAT TYPE OF COHERENT LIGHT SOURCE (AND THUS FOR EACH POSITION OF THAT TYPE OF COHERENT LIGHT SOURCE) THE LIGHT SOURCE ILLUMINATES THE SURFACE WHILE THE ONE OR MORE CAMERAS CAPTURE AN IMAGE OR IMAGES OF THE SURFACE

FOR EACH OF THE ONE OR MORE TYPES OF COHERENT LIGHT SOURCES, RESPECTIVELY, ALL OF THE LIGHT SOURCES IN THAT TYPE OF COHERENT LIGHT SOURCE (AND THUS ALL OF THE POSITIONS OF THAT TYPE OF COHERENT LIGHT SOURCE) ILLUMINATE THE SURFACE SIMULTANEOUSLY WHILE THE ONE OR MORE CAMERAS CAPTURE AN IMAGE OR IMAGES OF THE SURFACE

503

A COMPUTER (E.G. AN IC OR MICROCONTROLLER) (A) PERFORMS ONCHIP PROCESSING OF THE IMAGES TO EXTRACT PARAMETER VALUES AND (B) TRANSMITS THE PARAMETER VALUES BY A WIRED OR WIRELESS COMMUNICATION LINK TO A REMOTE COMPUTER.

505

THE REMOTE COMPUTER (A) PERFORMS A CLASSIFIER ALGORITHM THAT TAKES THE PARAMETERS AS INPUT AND THAT DETERMINES A CLASSIFICATION OF THE SURFACE, AND (B) BASED ON THAT CLASSIFICATION, OUTPUTS SIGNALS TO CONTROL THE CONTENT OF AN I/O DEVICE.

METHODS AND APPARATUS FOR SURFACE CLASSIFICATION

RELATED APPLICATIONS

This application is a non-provisional of, and claims the benefit of the filing date of, U.S. Provisional Patent Application No. 61/994,749, filed May 16, 2014, the entire disclosure of which is herein incorporated by reference.

FIELD OF TECHNOLOGY

The present invention relates generally to surface classification.

COMPUTER PROGRAM LISTING

Attached are two ASCII text files: (1) Classifier_Java_code.txt, created Dec. 13, 2014 with a size of about 9 KB; and (2) Microcontroller_code.txt, created Dec. 13, 2014 with a size of about 19 KB. Each of these two ASCII text files comprises source code for a prototype implementation of this invention. These two ASCII text files are each incorporated by reference herein.

SUMMARY

In illustrative implementations of this invention, one or more light sources illuminate a surface with incoherent light, and one or more light sources illuminate the surface with coherent light. A camera (e.g., a 30×30 pixel image sensor) captures images of the surface. The images are captured while the surface is illuminated with the incoherent light and while the surface is illuminated with the coherent light. One or more computers take, as input, data indicative of or derived from the images, and determine a classification of the surface. Based on the classification, the one or more computers output signals to control an I/O (input/output) device. These signals cause the I/O device to display content. What content is displayed depends, at least in part, on the classification. The classification and adjustment of the I/O device occurs in real time.

In illustrative implementations, multiple light sources illuminate a surface with multi-spectral, multi-directional illumination that varies in direction, wavelength, coherence and collimation, while a camera images the surface. The light sources and camera are housed in a small, lightweight, sensor device. A computer (e.g., an integrated circuit or microcontroller) onboard the sensor device extracts parameter values from the image stream captured by the camera. The onboard computer then transmits these parameter values, e.g., wirelessly to another (e.g., external) computer, which uses the parameter values to classify the surface in real time. The "onchip" processing by the onboard computer reduces the amount of data transmitted and enables real-time performance.

In some cases, the sensor device comprises a small, lightweight, handheld device. In other cases, this device is embedded in a mobile communication device, such as a smartphone or tablet computer.

In illustrative implementations, this invention accurately classifies a wide range of surfaces, including transparent surfaces, specular surfaces, surfaces without visible features, natural and artificial textures, printed patterns, and micro-dot patterns.

The inventors performed an experiment to test how accurately a prototype of this invention classifies surfaces. The prototype correctly classified a set of transparent materials approximately ninety-nine percent of the time.

The description of the present invention in the Summary and Abstract sections hereof is just a summary. It is intended only to give a general introduction to some illustrative implementations of this invention. It does not describe all of the details and variations of this invention. Likewise, the description of this invention in the Field of Technology section is not limiting; instead it identifies, in a general, non-exclusive manner, a field of technology to which exemplary implementations of this invention generally relate. Likewise, the Title of this document does not limit the invention in any way; instead the Title is merely a general, non-exclusive way of referring to this invention. This invention may be implemented in many other ways.

BRIEF DESCRIPTION OF THE DRAWINGS

FIG. 5 is a flowchart of a method of illuminating, imaging and classifying a surface.

In FIG. 8A, the device is held up to a side wall. In FIG. 8B, the device is help up to a top wall.

In FIG. 8C, the user is not wearing gloves, and the smartphone displays a normal GUI. In FIG. 8D, the user is wearing gloves, and the smartphone displays a GUI with larger icons and larger text.

The above Figures show some illustrative implementations of this invention, or provide information that relates to those implementations. However, this invention may be implemented in many other ways.

DETAILED DESCRIPTION

In illustrative implementations of this invention, a device accurately classifies surfaces in real-time, including specular, transparent surfaces, and surfaces without distinct or obvious features. Based on the classification, the device outputs control signals to control a user interface (UI). The UI is adjusted in a manner that depends, at least in part, on the computed classification.

Figure 1:
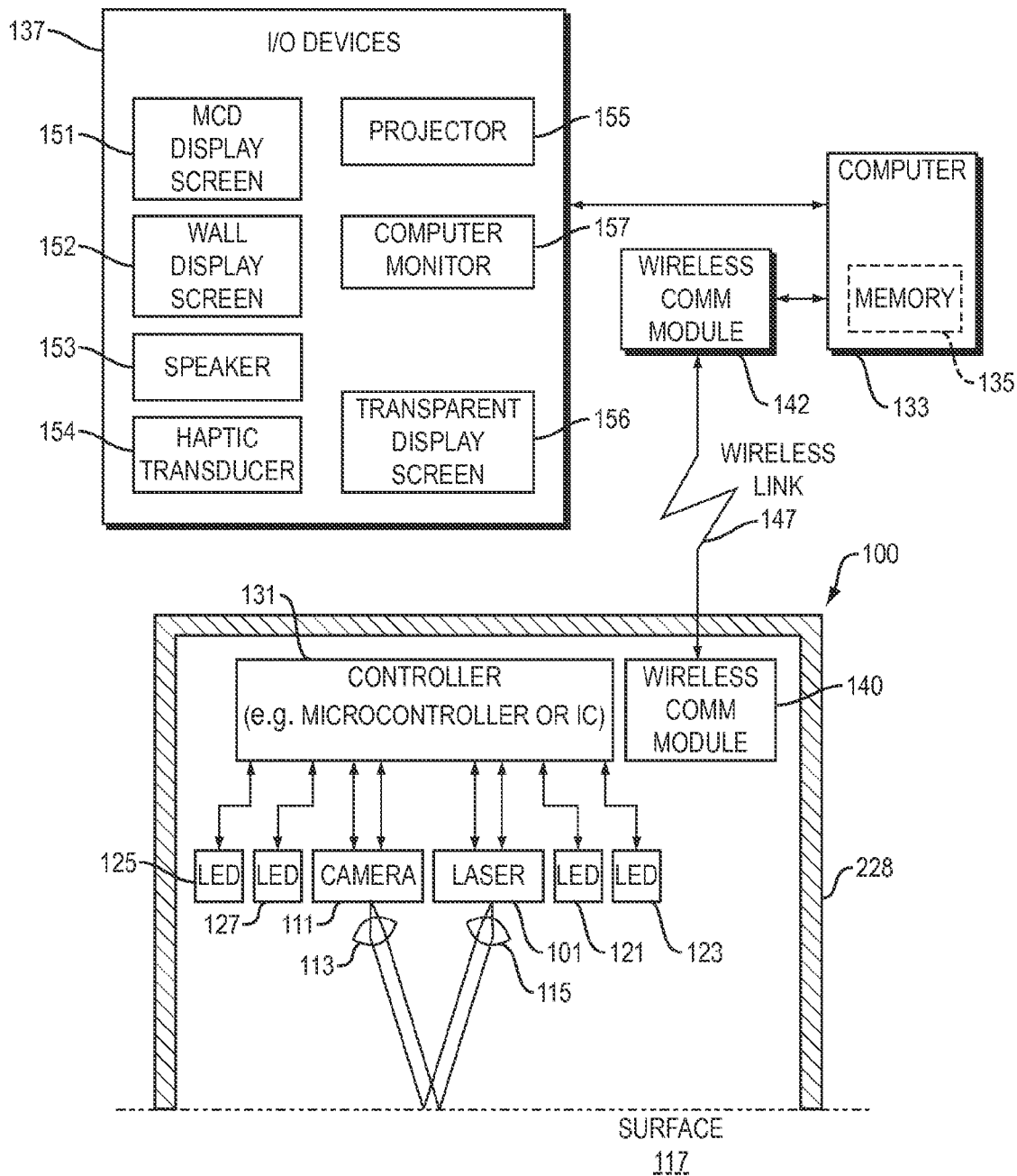
FIG. 1 is a diagram of an apparatus for surface classification.

FIG. 1 is a diagram of a device for surface classification, in an illustrative embodiment of this invention. In the example shown in FIG. 1, an onboard controller 131 (e.g., an integrated circuit) outputs signals to control light sources and a camera, such that the light sources emit light in a temporal sequence to illuminate a surface while the camera synchronously captures different images of the surface under different illumination patterns. The different illumination patterns that illuminate the surface in the temporal sequence vary in direction of illumination, spectrum of illumination (e.g., predominant color of light emitted by the respective light sources), and type of illumination (e.g., coherent or incoherent, and in some cases, collimated or uncollimated).

For example, in some cases, the onboard controller 131 controls both a camera and light sources, so that camera captures images under different illumination conditions.

In many cases, the onboard controller 131 causes the light sources to be turned on either (a) one color at a time, or (b) one light source at a time. In some cases, the controller 131 causes the light sources to be turned on one light source at a time. In the example shown in FIG. 1, the light sources comprise a laser 101 and four light-emitting diodes (LEDs). Two of the four LEDs 121, 125 have peak intensities at red (621 nm) and the other two LEDs 123, 127 have peak intensities at green (525 nm). Thus, light sources 121, 125 have a different spectral intensity than light sources 123, 125.

In some use scenarios, the controller 131 causes light sources to emit light in the following temporal sequence: (a) first a laser 101 emits light, while the other light sources are off, (b) then red LED 121 is on, while the other light sources are off; (c) then red LED 125 is on, while the other light sources are off; (c) then red LEDs 121, 125 are both on, while the other light sources are off; (d) then green LED 123 is on, while the other light sources are off; (c) then green LED 127 is on, while the other light sources are off; (c) then green LEDs 123, 127 are both on, while the other light sources are off.

The effect of this temporal sequence is that the direction, color and coherence of illumination of the light that is incident on the surface 117 changes over time.

This temporal sequence is repeated rapidly during operation of the apparatus 100. For example, in some cases, the light sources in apparatus 100 emit a temporal sequence of light of different types and from different directions, which sequence repeats rapidly (e.g., every 120 ms or less). Alternatively, only a single temporal sequence is performed.

Alternatively, different combinations of multiple light sources are on at different times during the temporal sequence, instead of only one light source at a time. Alternatively, the surface classification device includes multiple cameras (e.g. small image sensors) with different spectral response profiles (e.g., one camera is predominantly sensitive to red light, and another camera is predominantly sensitive to green light). For example, in some cases, multiple cameras capture images of a surface while all of the light sources are on simultaneously, thereby creating simultaneous multi-direction, multi-spectral, and multi-type (e.g., coherent and incoherent) illumination of the surface.

In some cases, the camera(s) capture multiple frames (exposures) in order to determine a classification of a surface. In other cases, the camera(s) take only a single exposure in order to classify a surface.

When the laser 101 is on, the laser 101 emits coherent light that passes through a collimating lens 115. Collimated, coherent light 107 exits lens 115, then travels to a surface 117, then reflects off of the surface 117, then passes through a lens 113 (e.g., a converging lens) and travels to a camera 111. For example, in some cases, camera 111 comprises a small (e.g., 30×30 pixel) image sensor. When the LEDs are on, the LEDs emit incoherent, uncollimated light.

Each of the light sources 101, 121, 123, 125, 127 is located in a different position. Thus, these light sources illuminate surface 117 from different directions.

In the example shown in FIG. 1, uncollimated light from the LEDs strikes the surface 117. Alternatively, collimating lens are placed in front of the LEDs and collimate the light from the LEDs, causing the LED light that strikes the surface 117 to be collimated.

In FIG. 1, camera 111 outputs signals that are indicative of visual data captured by the camera 111. Computer 131 analyzes this visual data and extracts parameter values. Data indicative of the parameter values is sent to a computer 133 via a wireless communication link 147. The wireless communication link 147 is between wireless communication modules 140, 142. (Alternatively, the parameter values are sent by a wired link). Computer 133 takes the parameter values as an input and classifies the surface 117 (e.g., as fur or a glove). In some cases, computer 133 performs machine learning. Computer stores data (e.g., data indicative of a training set) in memory 135.

Based on the computed classification, the computer 133 generates control signals for controlling one or more I/O devices 137. For example, in some cases, based on the computed classification of the surface, the computer 133: (a) controls images displayed by a computer monitor screen 157, by a screen of a mobile computing device (MCD) 151, by a wall display screen 152, by a projector 155, or by a transparent display screen 156; or (b) controls sounds produced by a speaker 153; or (c) controls haptic feedback produced by a haptic transducer 154.

In FIG. 1, the laser 103, light sources and controller 131 are housed in a sensor module 100. In some cases, the sensor module 100 comprises a small, lightweight, handheld device. In other cases, the sensor module 100 is embedded in a mobile communication device, such as a smartphone or tablet computer.

Figure 2:
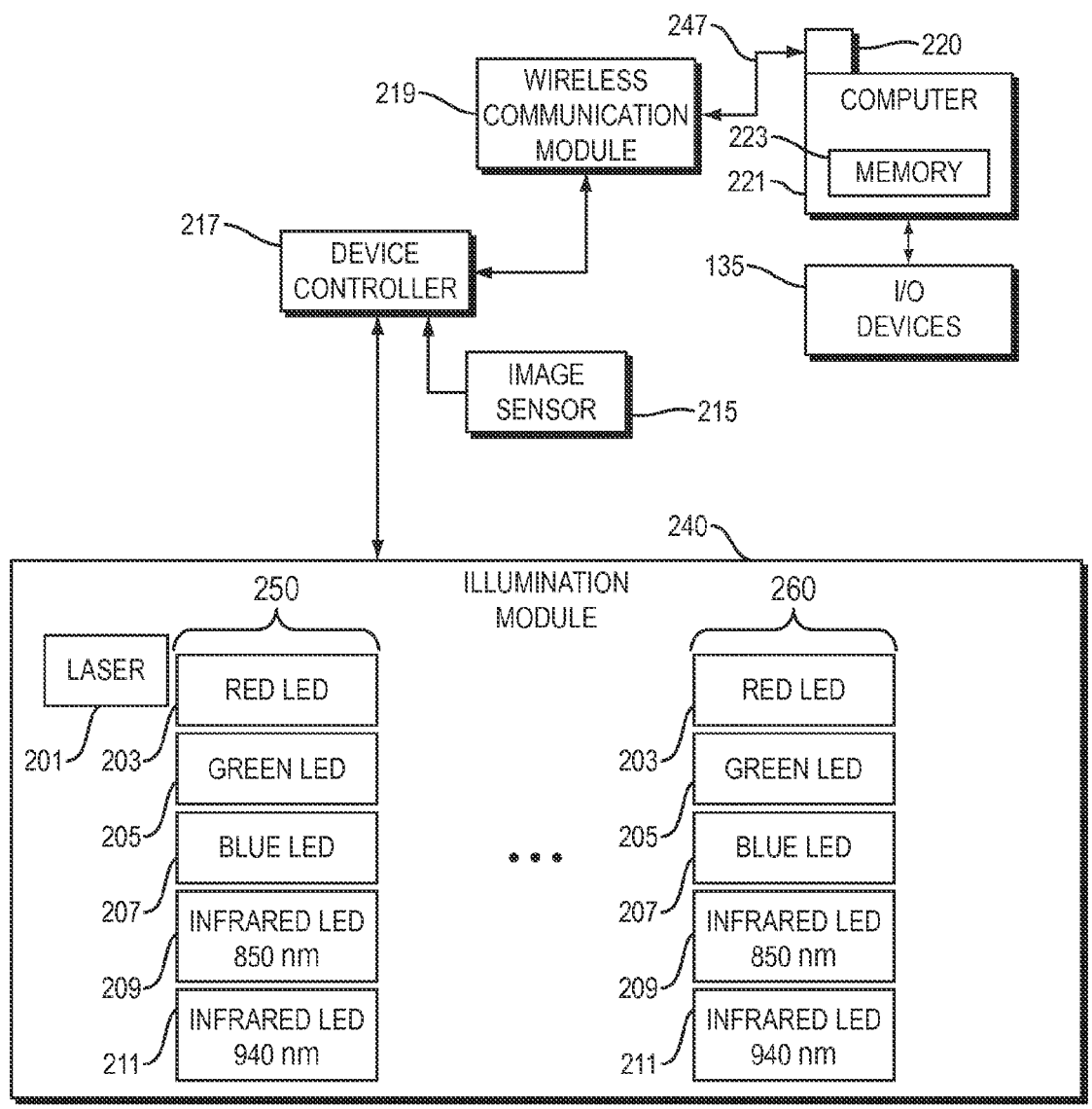
FIG. 2 is another block diagram of an apparatus for surface classification.

FIG. 2 is a block diagram of an apparatus for surface classification, in an illustrative implementation of this invention. In the example shown in FIG. 2, a device controller 217 controls an illumination module 240. The illumination module 240 comprises a laser 201, and multiple sets (e.g., 250, 260) of incoherent light sources. Each set of incoherent light sources (e.g., 250, 260) comprises five LEDs. The five LEDS are a red LED 203; a green LED 205, a blue LED 207; and two infrared LEDs 209, 211. The intensity of emitted light peaks at 621 nm for the red LED 203, at 525 nm for the green LED 205, at 475 nm for the blue LED, and at 940 nm and 850 nm for the two infrared LEDs, respectively. The device controller 217 also controls, and receives image data from, an image sensor (e.g., a camera) 215. The image sensor 215 images the surface that is being classified. In some cases, the device controller 217 comprises one or more microcontrollers, integrated circuits, or field-programmable gate arrays (FPGAs).

The number of sets (e.g., 250, 260) of light sources in the illumination module 240 may vary. For example, in some cases, there are two sets of light sources in the illumination module 240, and the total number of light sources in the illumination module is eleven (1 laser plus 10 LEDs). For example, in some cases, there are three sets of light sources in the illumination module 240, and the total number of light sources in the illumination module is sixteen (1 laser plus 15 LEDs).). For example, in some cases, there are four sets of light sources in the illumination module 240, and the total number of light sources in the illumination module is twenty one (1 laser plus 20 LEDs).

The position of the sets of light sources, and of the light sources within each set, may vary. This invention is not limited to any particular spatial positioning, number or spectral intensity (e.g., color) of light sources. The block diagrams in FIGS. 1 and 2 are conceptual; and do not attempt to portray actual spatial positions of the light sources.

In FIG. 2, the device controller 217 outputs control signals to cause the light sources (e.g., laser and LEDs) to produce multi-directional, multi-spectral, and multi-type (coherent and incoherent, and collimated and uncollimated) illumination. In some cases, the control signals cause the light sources to output a temporal sequence in which the spectral profile, direction, coherence and collimation of illumination of a surface changes over time. In some cases, in these temporal sequences, only one light source at a time is on. In other cases, in these temporal sequences, different combinations of light sources are on at different times.

In FIG. 2, the device controller 217 processes data from the image sensor, extracts parameter values from the data, and transmits the parameter values to a computer 221 via a wireless communication link 247. The wireless communication link 247 is between two wireless communication modules 219, 220. Alternatively, the device controller 217 transmits the parameter values to the computer 221 via a wired communication link.

The computer 221 analyzes the parameters and classifies the surface. For example, in some cases, the computer 221 classifies the surface as metal, fur or glass.

In illustrative implementations, the computer 221 performs one or more classification, clustering, pattern recognition or machine learning algorithms. For example, in order to classify a surface, the computer 221 in some cases performs a support vector machine algorithm, a neural network algorithm, a learning vector quantization algorithm, a linear classification algorithm (e.g., a Fisher's linear discriminant, logistic regression, or naive Bayes classifier), a quadratic classifier algorithm, a kernel estimation algorithm (e.g., a k-nearest neighbor algorithm), a boosting algorithm, a decision tree or random forest algorithm, a non-probabilistic classification algorithm, a probabilistic classification algorithm, a Bayesian classification algorithm, or a feature vector algorithm. The computer 221 stores data in memory 223. Based on the computed classification, the computer 221 generates control signals for controlling one or more I/O devices 135.

Figure 3:
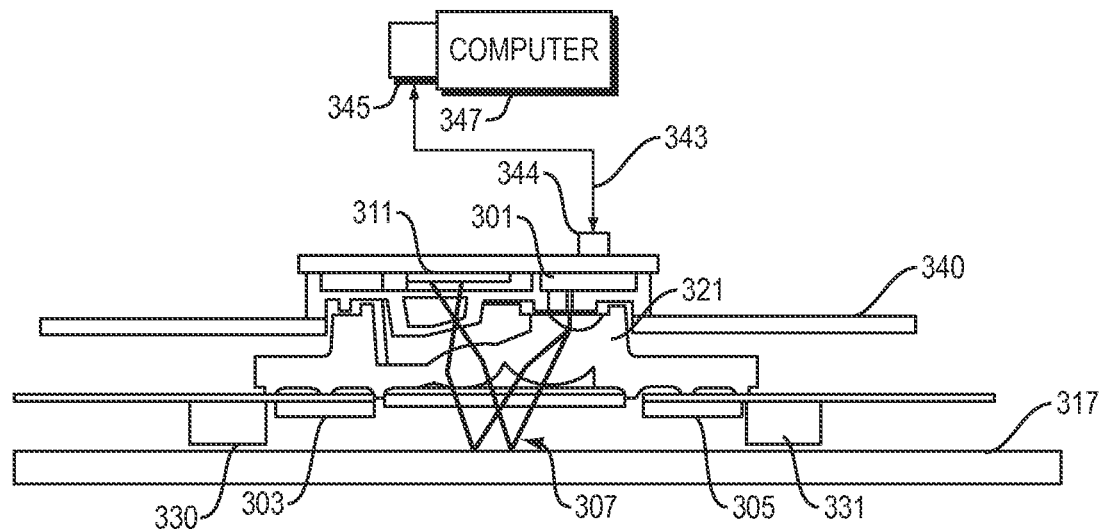
FIG. 3 is a diagram of a prototype of an apparatus for surface classification.

FIGS. 3 and 4 illustrate a prototype of this invention. The prototype shown in FIGS. 3 and 4 is a non-limiting example of this invention. This invention may be implemented in many other ways.

FIG. 3 is a diagram of a portion of the hardware of this prototype. The hardware includes a high-speed laser optical sensor (Avago® ADNS-9500) and small lens (Avago® ADNS-6190-002) 321. The sensor includes a vertical-cavity surface-emitting laser (VCSEL) 301, a lens 321, a high speed 30 pixel×30 pixel image sensor 311, and a device controller 340. The VCSEL laser 301 emits coherent light with 832-865 nm peak wavelength. A lens 321 then collimates this light. The lens 321 comprises a polycarbonate material. Collimated, coherent light 307 exits lens 321, then travels to a surface 317, then reflects off of the surface 317, then passes through another portion of lens 321 and travels to the image sensor 311. The image sensor 311 captures both visible and near-infrared light.

In this prototype, four sets of LEDs emit incoherent, uncollimated light. Two of the four sets of LEDs 303, 305 are shown in FIG. 2. Each set of LEDs includes five LEDs with a peak intensity at blue (475 nm), green (525 nm), red (621 nm), infrared (850 nm) and infrared (940 nm), respectively.

In this prototype, the device controller 340 outputs control signals to control the light sources (LEDs and laser) such that the light sources output light in a temporal sequence, as described in more detail in FIGS. 4A, 4B, 4C, 4D, 4E and 4F. In this prototype, the device controller 340 extracts four parameters from each frame captured by the camera 311: (a) average pixel intensity of the frame; (b) darkest pixel of the frame, (c) brightest pixel of the frame, and (d) surface quality. Surface quality is a measure of the number of valid feature points detected by the camera in the frame. Surface quality provides a useful index for roughness of the surface. The inventors experimentally determined that pixel intensity and surface quality are the best descriptors of material features, in this prototype.

By extracting these parameters, the number of bytes required to represent the data for a camera frame is reduced from about 900 bytes to four bytes. The device controller 340 sends these four bytes of data per camera frame via a wireless communication link 343 to a computer 347. By performing on-chip processing, and reducing the amount of data sent to the computer 347, the device controller 340 enables real-time surface classification. Wireless communication link 343 is between two wireless communication modules 344, 345. Alternatively, the device controller 340 transmits the parameter values to the computer 347 via a wired communication link.

In this prototype, in order to classify the surface 317, the computer 347 analyzes the parameters that were extracted by the device controller 340. The computer performs a support vector machine (SVM) classifier algorithm. To train the support vector machine, the computer 347 performs sequential minimal optimization (SMO), implemented in the Weka Toolkit. The features for the classifier algorithm are four parameters (surface quality, average pixel intensity, darkest pixel intensity and brightest pixel intensity) directly read from the sensor for each lighting configuration and shutter speed configuration. In total, there are 416 features (4 parameters×4 exposures×26 lighting patterns) for one data point.

Figure 4A:
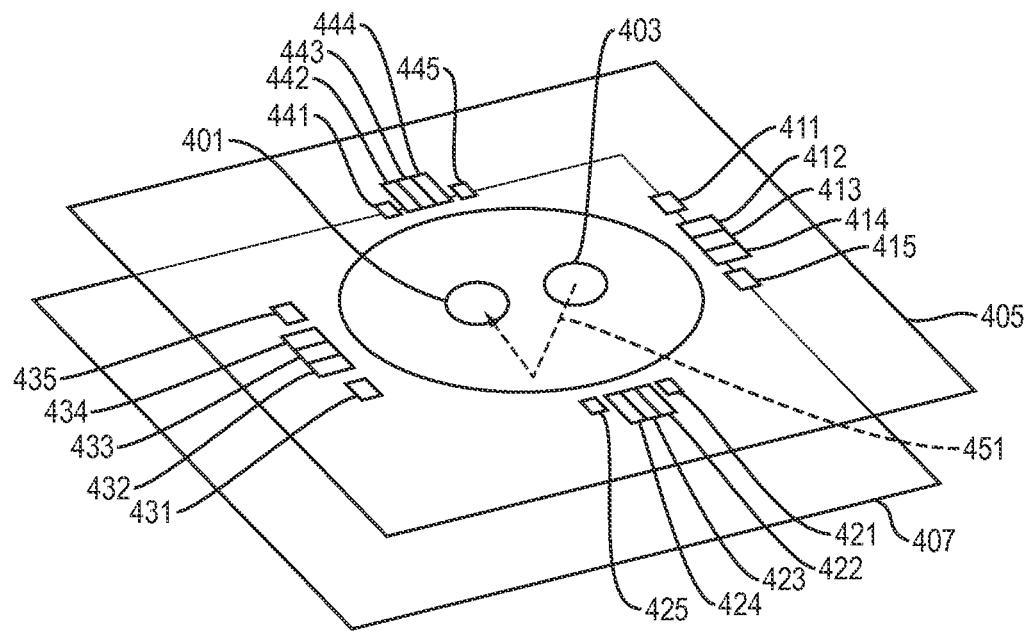
FIGS. 4A and 4B are diagrams that show light sources in the prototype.
Figure 4B:
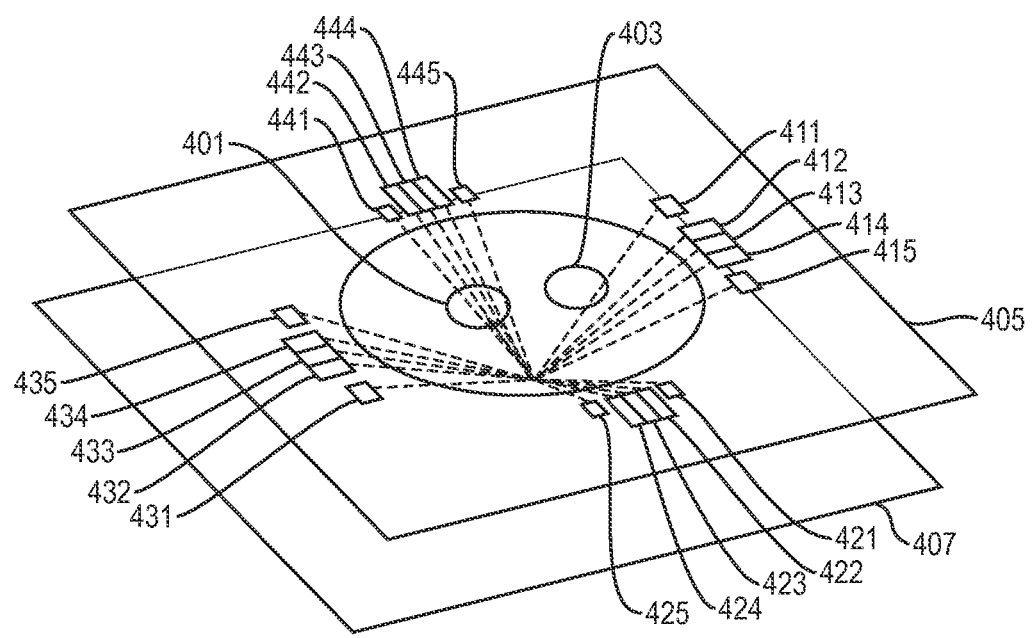

FIGS. 4A and 4B are diagrams that show light sources in the prototype. The light sources illuminate a surface from different directions and with different frequencies, coherence and collimation of light. In many cases, the light sources are turned on in a temporal sequence: First, in FIG. 4A, a laser illuminates the surface with coherent, collimated laser light, while LEDs are off. Then, in FIG. 4B, LEDs are turned on in a sequence, while the laser is turned off. For example, red LEDs are turned on one at a time, then all the red LEDS are turned on simultaneously, then green LEDs are turned on one at a time, then all the green LEDs are turned on simultaneously; then blue LEDs are turned on one at a time, then all the blue LEDS are turned on simultaneously, then infrared LEDs with a peak intensity of 850 nm are turned on one at a time, and then simultaneously, and then infrared LEDs with a peak intensity of 940 nm are turned on one at a time, and then simultaneously. In this example, lights that are not explicitly described as being on at a given time are off at the given time. The LEDs illuminate the surface with incoherent light. In most cases, the LED light is not collimated. In some cases, one or more collimating lenses collimate the LED light before the LED light strikes the surface that is being classified.

Alternatively, in some cases, a temporal sequence of different combinations of light sources illuminates the surface. Within each of these combinations of light sources, the light sources differ with respect to one or more of the following parameters: (a) spectral intensity (e.g., color); (b) spatial position, (c) coherence and (d) collimation.

As shown in FIGS. 4A and 4B, the light sources of the prototype comprise: a laser 403; four infrared LEDs with a peak intensity of 940 nm (411, 421, 431, 441); four red LEDs with a peak intensity of 621 nm (412, 422, 432, 442); four green LEDs with a peak intensity of 525 nm (413, 423, 433, 443); four blue LEDs with a peak intensity of 475 nm (414, 424, 434, 444); and four infrared LEDs with a peak intensity of 850 nm (415, 425, 435, 445). An image sensor 401 captures light that reflects from the surface being classified 407. For example, light 451 from the laser 403 strikes the surface 407 and then reflects to the image sensor 401. The reflected laser light forms a speckle pattern. The LEDs are housed in a printed circuit board 405.

Two versions of the prototype employ different Arduino-compatible 32-bit ARM microcontrollers: (a) a first version of the prototype includes a Teensy® 3.1 (Cortex®-M4, 96 MHz) microcontroller with Microchip® RN-42 Bluetooth module, and b) Spark Core (Cortex-M3, 72 MHz) with on-board WiFi module.

The prototype sensing system transmits data wirelessly to a computer. The prototype sensing system is roughly 60×60×40 mm, including a rechargeable battery. The optical part of the system (sensor chip, lenses, and LEDs) is roughly 20×18×11 mm. This small form allows the prototype to be embedded in handheld devices (e.g., smartphones), wearable devices, and the environment.

In this prototype, constant current regulator ICs (integrated circuits) set the LED driving current to 30 mA. In some use scenarios, the power consumption of the LEDs in the prototype is minimized by setting the same times for LED illumination and sensor exposure time.

In this prototype, a spacer (e.g., 330, 331) creates a constant distance between the surface being imaged and the image sensor.

In this prototype, the total number of lighting patterns are 26: (1 laser+5 wavelengths of LEDs)×(4 LED clusters+all LED clusters).

In this prototype, the frame rate of the image sensor is up to 11,750 frames per second (fps). However, in many use scenarios, the frame rate is set to manual shutter speed in order to capture multiple high dynamic range images to sense different material, from shiny metal to dark-colored fur and transparent glass.

In many use scenarios of this prototype, multiple exposures of the surface features are captured under controlled, high dynamic range conditions. To do so, the shutter speed is set for four fixed exposure periods: 0.83, 6.64, 53.12, and 424.96 ms.

In an illustrative use scenario of this prototype, the image sensor captures four features at four different exposure setups with 26 lighting conditions (416 features in total) in 117 ms.

In this prototype, on-chip computation of features of image makes these features available to microcontrollers at a low bandwidth, since there is no image transfer or image processing outside the sensor chip.

This invention is not limited to the prototype shown in FIGS. 3, 4A, 4B, 4C, 4D, 4E, and 4F. This invention may be implemented in many other ways.

FIG. 5 is a flowchart of a method of illuminating, imaging and classifying a surface, in an illustrative implementation of this invention. The method shown in FIG. 5 includes a step in which incoherent light sources illuminate a surface (Step 501); and a step in which one or more coherent light sources illuminate the surface (Step 503). The method shown in FIG. 5 also includes the following steps: A computer (e.g. an integrated circuit or microcontroller) performs onchip processing of the images to extract parameter values, and transmits the parameter values by a wired or wireless communication link to a remote computer. (Step 505). The remote computer performs a classifier algorithm that takes the parameters as input and that determines a classification of the surface. Based on that classification, the remote computer outputs signals to control the content of an I/O device. (Step 507)

In some implementations, an array of sets of lasers (VCSELs) are arranged in a spatially repeating pattern to create a wide-area sensor for surface classification.

Figure 6A:
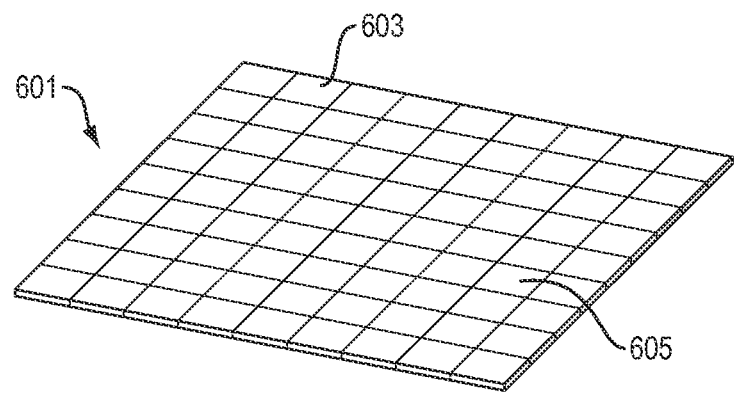
FIG. 6A is a perspective view of an array of VCSEL lasers, used in a wide area system for surface classification.

FIG. 6A is a perspective view of an array 601 of sets of VCSEL lasers, in an illustrative implementation. In the example shown in FIG. 6A, these sets of VCSEL are components in a wide-area sensor for surface classification. For example, regions 603 and 605 each include an array of VCSEL lasers.

Figure 6B:
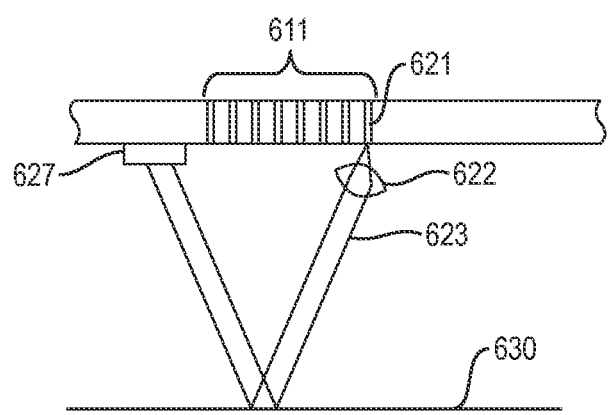
FIG. 6B is a diagram of a portion of a wide-area system for surface classification.

FIG. 6B is a diagram of a portion of a wide-area system for surface classification, in an illustrative implementation. In FIG. 6B, a set of VCSELs 611 includes multiple lasers, such as VCSEL 621. In the example shown in FIG. 6B, VCSEL 621 is emitting coherent light. A collimating lens 622 collimates the light from the VCSEL. The collimated, coherent light 623 strikes a surface 630 (which is being classified) and reflects to a camera 627.

Figure 7:
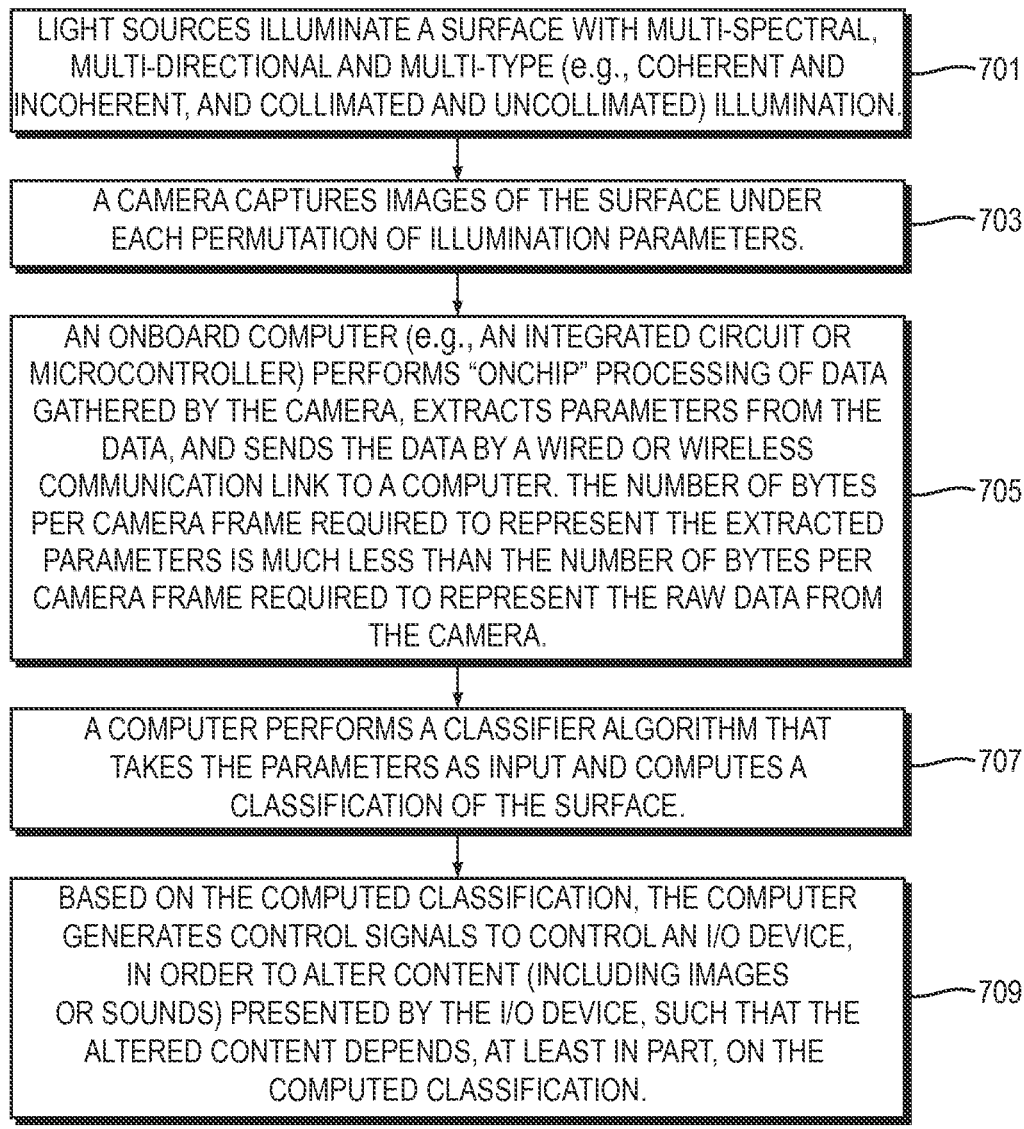
FIG. 7 is a flow chart that shows steps in a method for surface classification.

FIG. 7 is a flowchart of a method for surface classification, in an illustrative implementation. The method in FIG. 7 includes the following steps. Light sources illuminate a surface with multi-spectral, multi-directional and multi-type (e.g., coherent and incoherent, and collimated and uncollimated) illumination (Step 701). A camera captures images of the surface under each permutation of illumination parameters (Step 703). An onboard computer (e.g., an integrated circuit or microcontroller) performs "onchip" processing of data gathered by the camera, extracts parameters from the data, and sends the data by a wired or wireless communication link to a computer. The number of bytes per camera frame required to represent the extracted parameters is much less than the number of bytes per camera frame required to represent the raw data from the camera (Step 705). A computer performs a classifier algorithm that takes the parameters as input and outputs a classification of the surface (Step 707). Based on the classification, the computer generates control signals to control one or more I/O devices, in order to alter content (including images or sounds) presented by the I/O devices, such that the altered content presented by the I/O devices depends, at least in part, of the computed classification (Step 709)

Figure 8B:
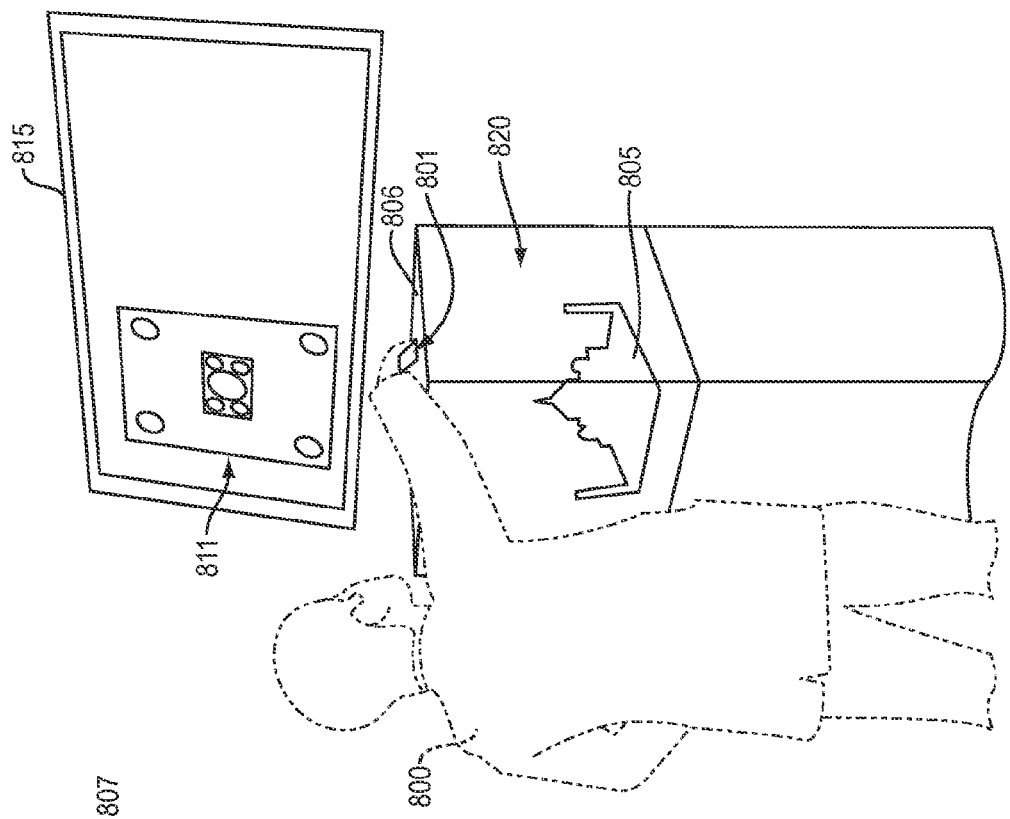
FIGS. 8A and 8B show a use scenario, in which a surface classification device identifies different transparent walls of a showcase.
Figure 8A:
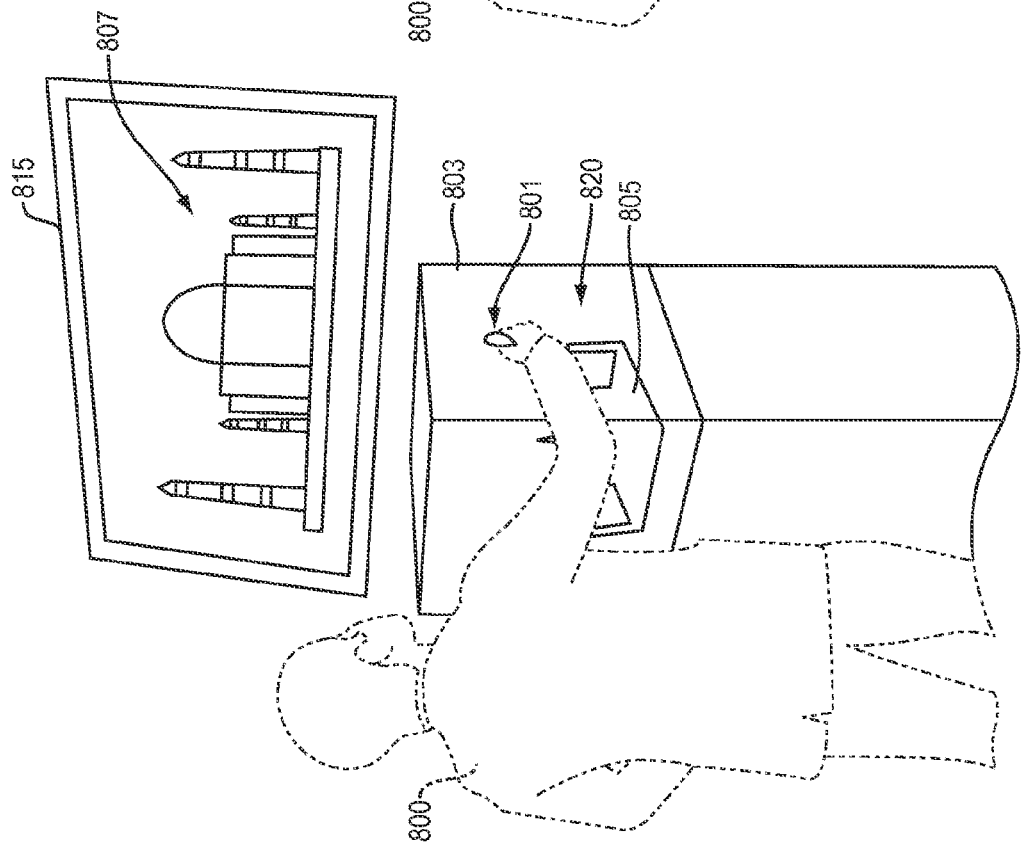

FIGS. 8A and 8B show use scenarios, in which a surface classification device 801 identifies different transparent walls of a six-walled, cube-shaped, transparent showcase 820. The transparent walls of the showcase 820 encode data that is invisible to the unaided human eye, but that is detectable by the surface classification device 801. The encoded data uniquely identifies each wall. For example, in some cases, the encoded data is simply that each of the walls comprises a different transparent material. Or, in some cases, the encoded data comprises tiny features that have different material properties than the wall to which they are attached or in which they are embedded. For example, in some cases, the materials used in different walls of the showcase 820 or in different tiny features of the wall comprise two or more of the following: polyethylene terephthalate glycol-modified (PETG), polyvinyl chloride (PVC), cast acrylic, cellulose acetate, extruded acrylic, glass, or polycarbonate. In some cases, the encoded data comprises tiny features that have distinctive shapes or that are arranged in a distinctive pattern.

In the examples shown in FIGS. 8A and 8B, the showcase 820 contains a miniature physical model 805 of the Taj Mahal. A user 800 holds a surface classification device 801 against a transparent side wall 803 and a transparent top wall 806, respectively, of the showcase 820. The device 801 detects encoded data in the transparent walls. Based on the encoded data, the device 801 outputs control signals that control an I/O device (a wall-mounted electronic display screen) 815, causing different images to be displayed by the I/O device 815, depending on which wall of the showcase is detected by device 801. In FIG. 8A, the device 801 detects a side wall 803 of the showcase and causes a side view 807 of the Taj Mahal to be displayed by the I/O device 815. In FIG. 8B, the device 801 detects a top wall 806 of the showcase, and causes a top view 811 of the Taj Mahal to be displayed by the I/O device 815.

In an alternate use scenario, a surface classification device is housed onboard a smartphone. The smartphone is held up against different transparent walls of the six-walled showcase 820, and the surface classification device onboard the smartphone identifies the walls. Depending on which wall is identified, the screen of the smartphone displays different content. For example, in some use scenarios: (a) if a top wall of the showcase is detected, the smartphone screen displays a blueprint of a Wright Flyer biplane; (b) if the left or right side walls of the showcase are detected, the smartphone screen displays video of the biplane flying; and (c) if the front or back walls of the showcase are detected, the smartphone screen displays animation explaining how the engine and propeller of the biplane work.

Figure 8C:
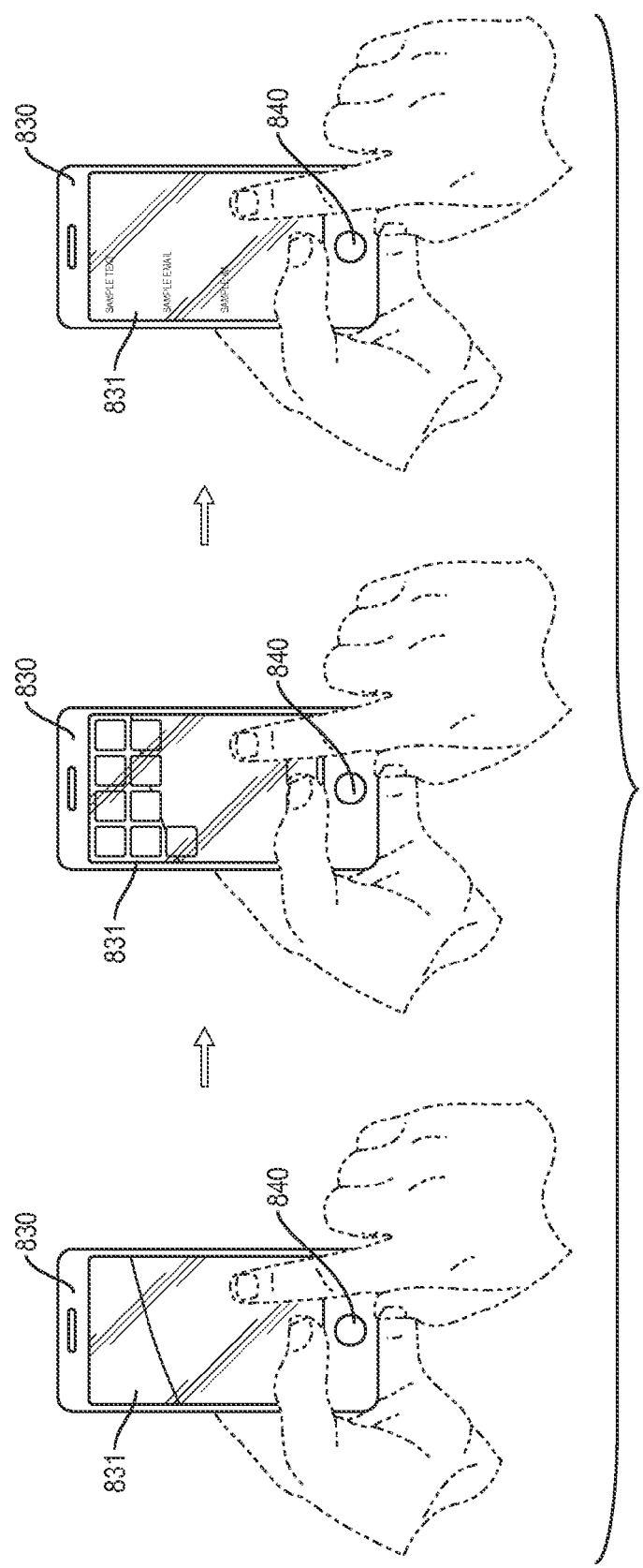
FIGS. 8C and 8D show a use scenario, in which a surface classification device in a smartphone detects when a user is wearing gloves, and changes the display of a graphical user interface accordingly.
Figure 8D:
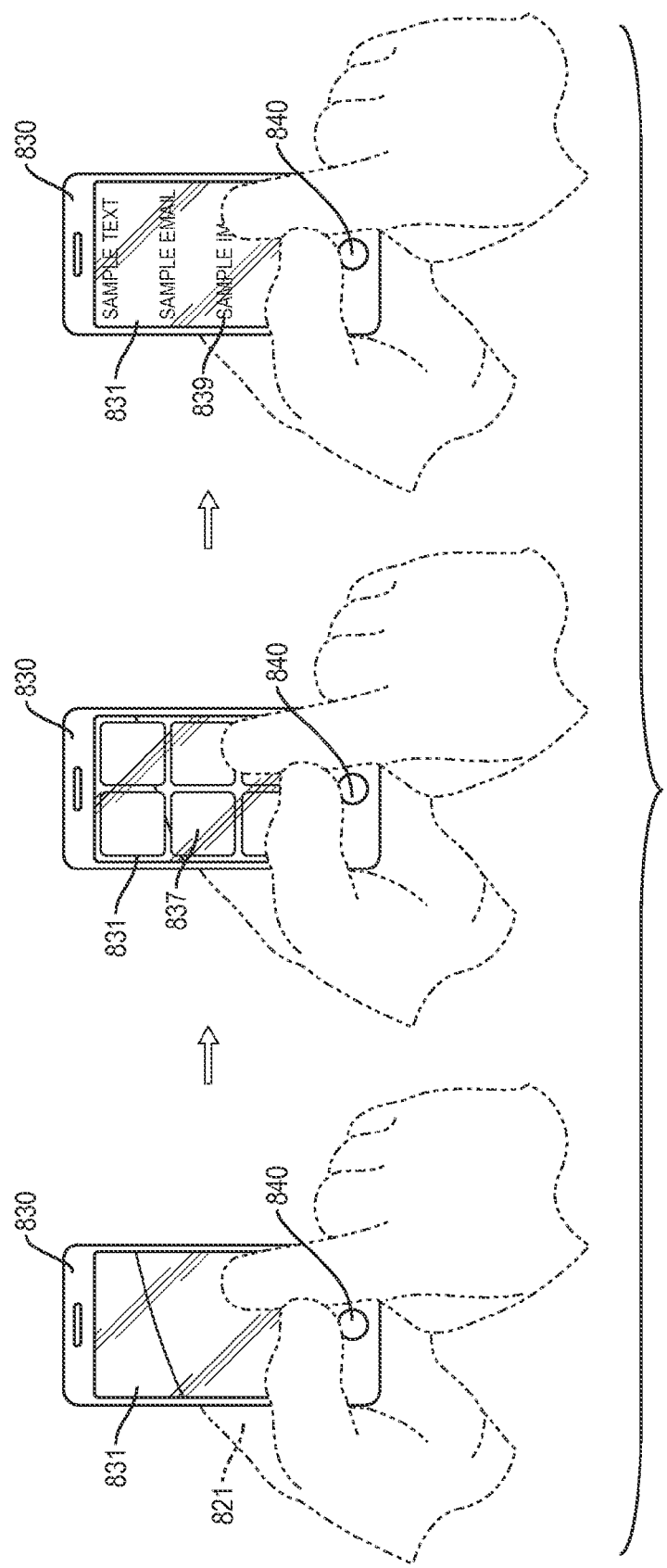

FIGS. 8C and 8D show use scenarios, in which a classification device is embedded in a home button 840 of a smartphone 830. The classification device detects when a user is wearing gloves, and changes the display of the smartphone's graphical user interface accordingly. In FIG. 8A, the user has previously touched the home button 840 with his or her finger, while not wearing gloves. The classification device in the home button 840 classifies the surface finger as skin, and a screen 831 in the smartphone 830 displays a normal user interface, including normal size virtual buttons 833 and normal size text 835 and spacing between text. In FIG. 8B, the user has previously touched the home button 840 with his or her finger, while wearing a pair of gloves 821 that cover the finger. The classification device in the home button 840 classifies the glove that touched the home button in a category other than skin (e.g., textile or leather), and causes a screen 831 in the smartphone 830 to adjust the user interface accordingly. Specifically, the screen displays a modified user interface, including larger virtual buttons 837 and larger size text 839.

In some cases, the surface (e.g., 117 or 317) that is identified by the surface classification device comprises a transparent sheet. For example, in some cases, different transparent sheets are placed at different times over an optical mouse pad or over a mobile computing device (e.g., smartphone or tablet computer). The surface classification device recognizes which transparent sheet is present, and based on that recognition, alters a user interface or other images presented by an I/O device. For example, in some cases: (a) the surface classification device is embedded in an optical mouse; and (b) depending on which transparent sheet is detected over an optical mouse pad, the surface classification device causes a computer monitor (e.g., 157) to alter a viewport display of a CAD program. In other cases, (a) the surface classification device is embedded in a tablet computer; and (b) depending on which transparent sheet is detected over the tablet computer, the surface classification device causes the tablet computer to display different types of data. For example, in some cases: (a) if a first type of transparent sheet is detected over a tablet computer, the tablet displays detailed information regarding inventory in stock (e.g., number of items in stock, breakdown costs, profit ratio and remarks only for sales personnel); and (b) if a second type of transparent sheet is detected over a tablet computer, the tablet computer displays only redacted information, such as the sales price per item.

Evaluation of Prototype

The inventors have performed an experiment to test the accuracy of the above prototype (that is, the prototype described in FIGS. 3 and 4 and the accompanying text).

The experiment tested the ability of the prototype to accurately classify three types of surfaces: transparent material, synthetic animal fur and skin, and surfaces typically found in home and office environments. Specifically, the experiment tested the ability of the prototype to accurately classify: (a) nine transparent materials, which were polyethylene terephthalate glycol-modified (PETG), polyvinyl chloride (PVC), cast acrylic, cellulose acetate, extruded acrylic, glass, microscope slide, polycarbonate, and air (no material); (b) five synthetic animal furs and skins from a picture book, which were lion fur, panda fur, iridescent colored lizard skin, elephant skin, and zebra fur, and (c) seven materials from office and living spaces, which were office desk, aluminum laptop palm rest, chair seat (fabric), chair arm rest (rubber), fabric mouse pad, plastic mouse pad, and carpet.

In the experiment, data capture was done by placing the sensor on top of the surface sample. For each sample, 20 data instances were captured while moving the sensor gently over the surface. This process was repeated five times for all of the materials. In total, 100 samples were obtained for each material.

The experiment was conducted in an ordinary office environment with fluorescent ambient lighting. In the experiment, the transparent surfaces were cleaned with lens cleaning wipes before being imaged by the surface classifier device.

In the experiment, a ten-fold cross validation for three scenarios was performed independently to evaluate how accurately the prototype classifies the materials. The average correct classification rate for the respective materials, under ten different active lighting conditions, is shown in FIGS. 9A, 9B, and 9C.

Figure 9A:
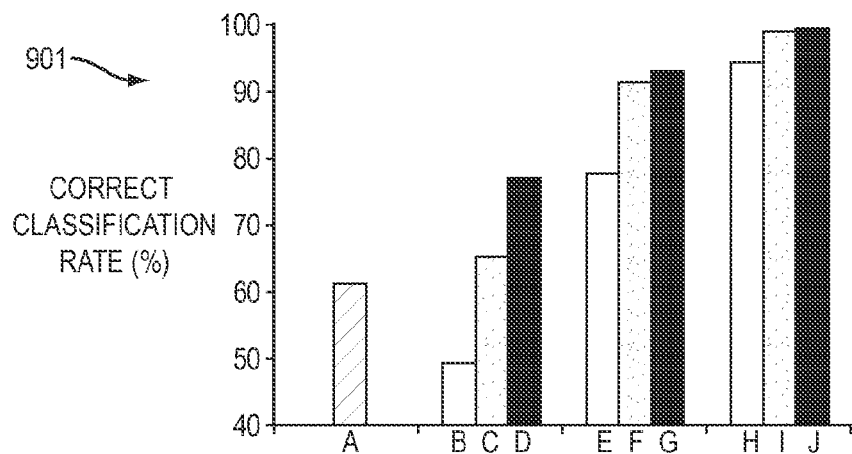
FIGS. 9A, 9B and 9C are bar charts summarizing experimental data regarding the accuracy of a prototype under ten different lighting conditions. The bar charts in FIGS. 9A, 9B, and 9C summarize the prototype's accuracy when classifying (a) transparent materials, (b) synthetic animal fur and skin, and (c) office/home materials, respectively.
Figure 9B:
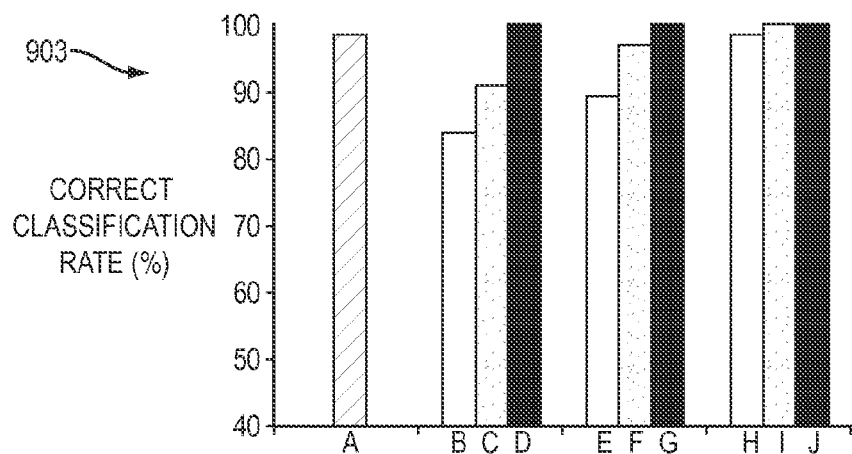
Figure 9C:
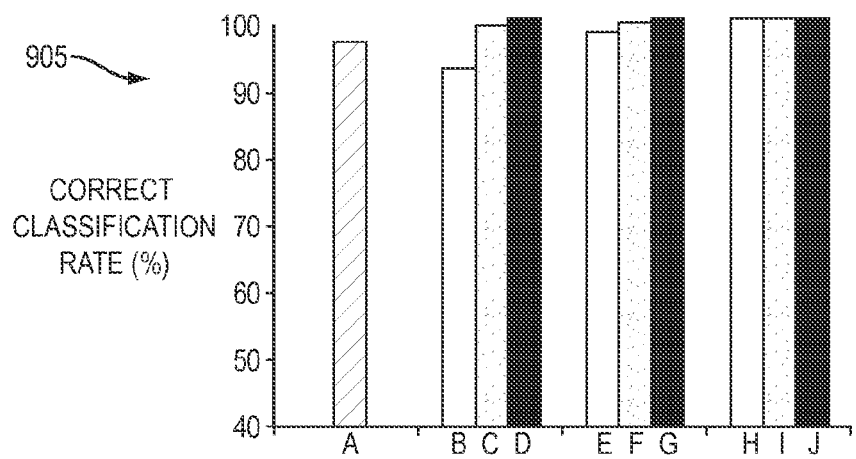

FIGS. 9A, 9B and 9C are bar charts summarizing the results of the experiment: Specifically, these bar charts summarize the accuracy of the prototype, under ten different lighting conditions, as measured in the experiment. The bar chart 901 in FIG. 9A summarizes the prototype's accuracy when classifying transparent materials. The bar chart 903 in FIG. 9B summarizes the prototype's accuracy when classifying synthetic animal fur and skin. The bar chart 905 in FIG. 9C summarizes the prototype's accuracy when classifying materials found in office and living spaces.

In FIGS. 9A, 9B, and 9C, the vertical axis is percentage of correct classifications. The horizontal axis lists ten different active lighting conditions (A through J).

Figure 10:
FIG. 10 is a chart that identifies the ten lighting conditions that were used in the tests summarized in FIGS. 9A, 9B and 9C.

FIG. 10 is a chart that identifies the active ten lighting conditions (labeled A to J) 1000 that were employed in the tests summarized in FIGS. 9A, 9B and 9C. For example: (a) lighting condition "A" means illumination by only a single laser; (b) lighting condition "B" means illumination by only a single IR-850 nm LED; (c) lighting condition "C" means illumination by only a single cluster of LEDs; (d) lighting condition "D" means illumination by only a laser and a single cluster of LEDs; (e) lighting condition "E" means illumination by only two IR-850 nm LEDs; (f) lighting condition "F" means illumination by only two clusters of LEDs; (g) lighting condition "G" means illumination by only a laser and two clusters of LEDs; (h) lighting condition H means illumination by only four IR-850 nm LEDs; (i) lighting condition "I" means illumination by only four clusters of LEDs; and (J) lighting condition "J" means illumination by only a laser and four clusters of LED. In lighting conditions C-J, the light sources are turned on and off in a temporal sequence. During part of the temporal sequence, light sources are turned on one light source at a time, while the other light sources are off. During another part of the temporal sequence, each set of light sources that has the same spectral intensity is turned on simultaneously (e.g., all red LEDs are turned on simultaneously), while the other light sources are kept off. As used in this paragraph, a "cluster" of LEDs means a set of five LEDs that consists of an AR-850 nm LED, red LED, green LED, blue LED and AR-940 nm LED. As used in this paragraph: "AR-850 nm LED" means an LED with a peak intensity of 850 nm; "red LED" means an LED with a peak intensity of 621 nm; "green" LED" means an LED with a peak intensity of 525 nm; "blue LED" means an LED with a peak intensity of 475 nm; and "AR-940 nm LED" means an LED with a peak intensity of 940 nm;

FIGS. 9A, 9B and 9C show that the prototype achieved a high recognition rate (above 99.0%) on average for all of the materials, when all lighting directions and spectra were considered. Setup C roughly mimics a simple multi-spectrum LED method. The experimental data summarized in FIGS. 9A, 9B and 9C indicates that, as a general trend, greater variance in lighting directions and more spectral configurations will produce higher classification accuracy. For transparent materials, the simple non-directional multi-spectrum LED sensing C showed a low correct classification rate of 65.44%, which tends to confirm the desirability of the multi-directional, multi-spectral setup. By adding laser to the illumination, correct classification rates increase as seen in FIGS. 9A, 9B and 9C.

In some cases, one or more tangible, non-transitory machine-readable media are employed. Each machine-readable medium stores instructions for one or more computers to perform any calculation, computation, program, algorithm, computer function or computer task described or implied in this document. For example, the stored instructions include instructions for an onboard computer to control light sources and a camera, to extract parameter values from a stream of raw visual data from the camera, and to wirelessly send the parameter values to another computer. For example, the stored instructions also include instructions for the other computer to classify the surface and to output control signals to adjust the display of an I/O device, based at least in part of the computed classification.

More Details

Figure 11:
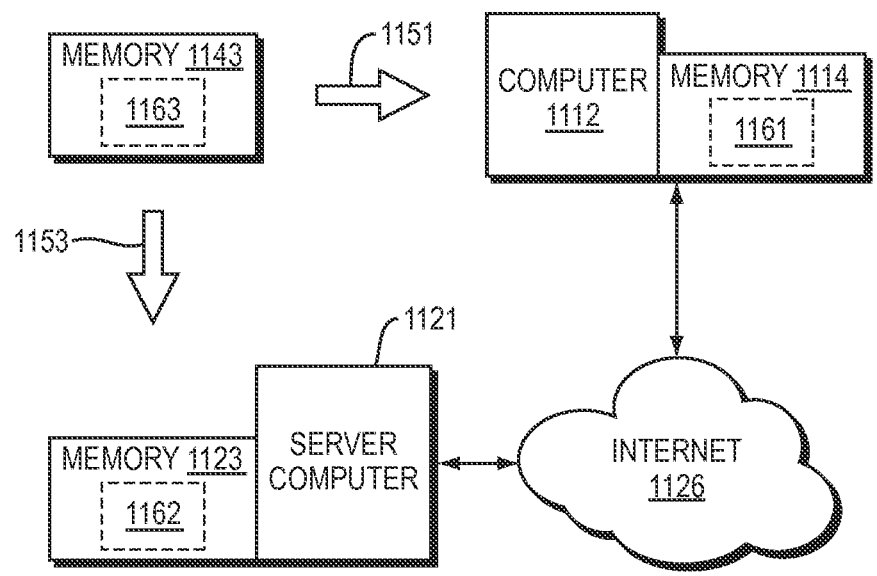
FIG. 11 shows three examples of machine-readable media.

In the example shown in FIG. 11, three non-transitory machine-readable media 1161, 1162, 1163 store identical copies of this program. Thus, each of the machine-readable media 1161, 1162, 1163 stores the instructions for this program.

In FIG. 11, machine-readable medium 1161 is part of memory device 1114 for computer 1112. Computer 1112 executes the program, classifies a surface, and outputs signals to control an I/O device to display content, which content is a determined, at least in part, by the classification.

In FIG. 11, machine-readable medium 1162 is part of memory device 1123, which is part of, or auxiliary to, server computer 1121. Server computer 1121 is connected to the Internet 1126. In some cases, the program is downloaded from the server computer via the Internet 1126. For example, in some cases, the download involves transferring a copy of the encoded program instructions from machine-readable medium 1162 to server computer 1121, then over the Internet 1126 to computer 1112, and then to machine-readable medium 1161, which is part of memory device 1114.

In FIG. 11, machine-readable medium 1163 comprises all or part of a memory device 1143. For example, in some cases, machine-readable medium 1163 stores a master copy or backup copy of the encoded program instructions. In some cases, the program instructions encoded in the master copy are copied 1151 into machine-readable medium 1161 during manufacturing. In some cases, the program instructions encoded in the master copy are copied 1153 into machine-readable medium 1162, which is used in downloading the program, as discussed above.

In some cases, a non-transitory, machine-readable medium (e.g., 1161, 1162, or 1163) comprises part or all of an electronic memory storage device, such as a RAM (random-access memory), DRAM (dynamic random-access memory), ROM (read only memory), PROM (programmable read only memory), EPROM (erasable programmable read only memory), or EEPROM (electrically erasable programmable read only memory) device; and (b) the program is encoded in voltage levels in a set of electronic components (e.g., flip-flops or latches) in the medium. In some cases: (a) voltage levels in hardware components of the machine-readable medium encode a set of logic states that do not change throughout an entire time interval that has a non-zero duration, and (b) the hardware components of the machine-readable medium exist throughout this entire time period. Alternatively, a machine-readable medium (e.g., 1161, 1162, or 1163) comprises part or all of a CD-ROM or other optical disc storage device, and a computer reads data or instructions stored in the CD-ROM by using an optical disc driver.

Figure 12:
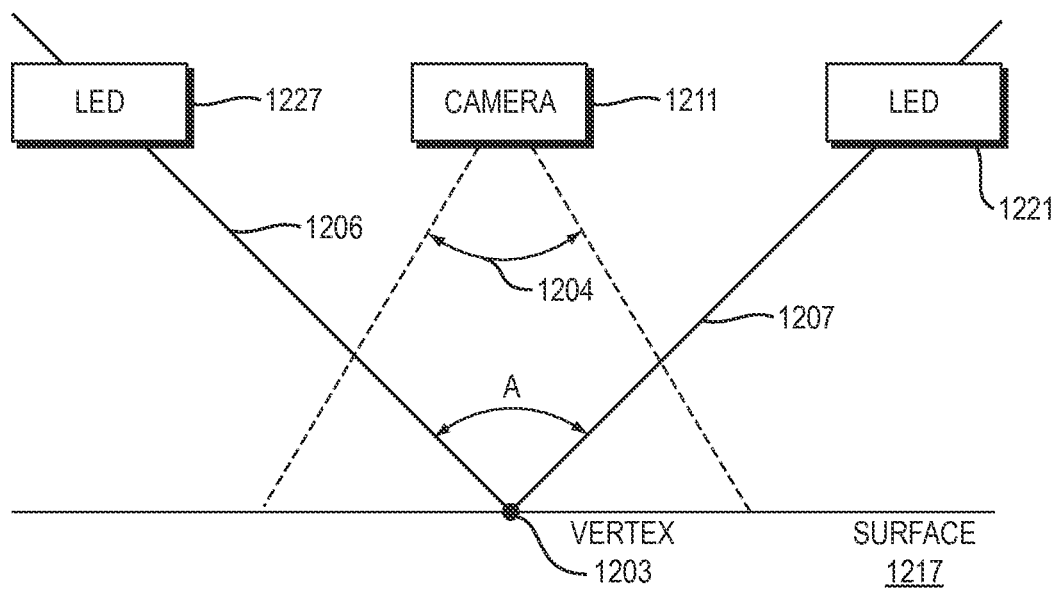
FIG. 12 shows an example of multi-directional illumination.

FIG. 12 shows an example of multi-directional illumination, in an illustrative implementation of this invention. In FIG. 12, two LEDs 1227, 1221 illuminate a surface 1217. A point 1203 on the surface 1217 is in the field of view 1204 of the camera 1211. The point 1203 is the vertex of an angle A. The angle A is formed by two lines 1206, 1207 from the point 1203 to the two LEDs 1227, 1221, respectively. The angle A is at least thirty degrees.

Computers

In exemplary implementations of this invention, one or more electronic computers (e.g. 131, 133, 217, 221, 340, 347) are programmed and specially adapted: (1) to control the operation of, or interface with, hardware components of a surface classification device, including light sources, a camera, a controller, and one or wireless communication modules; (2) to control light sources and a camera, to extract parameter values from a stream of raw visual data from the camera, to classify a surface and to output control signals to adjust the display of an I/O device, based at least in part of the computed classification; (3) to perform any other calculation, computation, program, algorithm, computer function or computer task described or implied above; (4) to receive signals indicative of human input; (5) to output signals for controlling transducers for outputting information in human perceivable format; and (6) to process data, to perform computations, to execute any algorithm or software, and to control the read or write of data to and from memory devices. The one or more computers may be in any position or positions within or outside of the surface classification device. For example, in some cases (a) at least one computer is housed in or together with other components of the surface classification device, such as the imaging sensor, and (b) at least one computer is remote from other components of the surface classification device. The one or more computers are connected to each other or to other components in the device camera either: (a) wirelessly, (b) by wired connection, or (c) by a combination of wired and wireless links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, computer function or computer task described or implied above. For example, in some cases, instructions encoded in a tangible, non-transitory, computer-accessible medium comprise instructions for a computer to: (1) to control the operation of, or interface with, hardware components of a surface classification device, including light sources, a camera, a controller, and one or wireless communication modules; (2) to control light sources and a camera, to extract parameter values from a stream of raw visual data from the camera, to classify a surface and to output control signals to adjust the display of an I/O device, based at least in part of the computed classification; (3) to perform any other calculation, computation, program, algorithm, computer function or computer task described or implied above; (4) to receive signals indicative of human input; (5) to output signals for controlling transducers for outputting information in human perceivable format; and (6) to process data, to perform computations, to execute any algorithm or software, and to control the read or write of data to and from memory devices.

Network Communication

In illustrative implementations of this invention, an electronic device (e.g., computer 131, 133, 217, 221, 340 or 347) is configured for wireless or wired communication with other electronic devices in a network.

For example, in some cases, one or more computers (e.g., 131, 133, 217, 221, 340 or 347 each include a wireless communication module for wireless communication with other electronic devices in a network. Each wireless communication module (e.g., 140, 142, 219, 220, 344, 345) includes (a) one or more antennas, (b) one or more wireless transceivers, transmitters or receivers, and (c) signal processing circuitry. The wireless communication module receives and transmits data in accordance with one or more wireless standards.

In some cases, one or more of the following hardware components are used for network communication: a computer bus, a computer port, network connection, network interface device, host adapter, wireless module, wireless card, signal processor, modem, router, computer port, cables or wiring.

In some cases, one or more computers (e.g., onboard the same support structure as the sensor module) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Computer Program Listing

Two files are listed in the Computer Program Listing above.

The Microcontroller_code.txt file encodes instructions for a computer to: (a) communicate with the image sensor and control the laser and LED lightings; (b) receive commands from a main computer; (c) receive feature information from the image sensor; (d) change lighting conditions (e.g., direction and color of LEDs, or switch to laser illumination); and (e) change shutter speed, including to capture feature data at multiple shutter speeds (exposure times), including to gather High Dynamic Range data.

The Classifier_Java_code.txt encodes instructions for a computer to: (a) send commands to the micro-controller; (b) receive feature data from the micro-controller; (c) create a machine learning classifier from the collected feature data; (d) run a classifier to recognize the various surfaces; and (f) send out commands to other software to run applications such as controlling other devices or changing images to display.

This invention is not limited to the software set forth in these two ASCII text files. Depending on the particular implementation, the software used in this invention may vary.

DEFINITIONS

The terms "a" and "an", when modifying a noun, do not imply that only one of the noun exists.

Non-limiting examples of a "camera" include: (a) a digital camera; (b) a video camera; (c) an image sensor, (d) an optical instrument that records images; (e) a light sensor; or (f) a set or array of light sensors. The term "camera" includes any computers that process data captured by the camera.

To compute "based on" specified data means to perform a computation that takes the specified data as an input.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

"Emission spectrum" means a spectrum of light emitted by a light source.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

The term "for instance" means for example.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure or radiant energy density.

"I/O device" means an input/output device. For example, an I/O device includes any device for (a) receiving input from a human, (b) providing output to a human, or (c) both. For example, an I/O device includes a user interface, graphical user interface, keyboard, mouse, touch screen, microphone, handheld controller, display screen, speaker, or projector for projecting a visual display. Also, for example, an I/O device includes any device (e.g., button, dial, knob, slider or haptic transducer) for receiving input from, or providing output to, a human.

"Light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

The term "mobile computing device" or "MCD" means a device that includes a computer, a camera, a display screen and a wireless transceiver. Non-limiting examples of an MCD include a smartphone, cell phone, mobile phone, tablet computer, laptop computer and notebook computer.

The term "or" is inclusive, not exclusive. For example A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

As used herein, the term "set" does not include a group with no elements. Mentioning a first set and a second set does not, in and of itself, create any implication regarding whether or not the first and second sets overlap (that is, intersect).

"Some" means one or more.

"Spectral sensitivity profile" means intensity of light recorded by a camera, as a function of wavelength of the light.

"Spectrum" means light intensity as a function of wavelength of the light.

As used herein, a "subset" of a set consists of less than all of the elements of the set.

"Substantially" means at least ten percent. For example: (a) 112 is substantially larger than 100; and (b) 108 is not substantially larger than 100.

The term "such as" means for example.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, Applicant is acting as Applicant's own lexicographer.

Variations:

This invention may be implemented in many different ways. Here are some non-limiting examples:

In one aspect, this invention is a method comprising, in combination: (a) a first set of one or more light sources illuminating a surface with incoherent light; (b) a second set of one or more light sources illuminating the surface with coherent light; and (c) one or more cameras capturing images of the surface while the surface is illuminated with the incoherent light and while the surface is illuminated with the coherent light; and (d) one or more computers (i) taking, as input, data indicative of or derived from the images, (ii) determining a classification of the surface, and (iii) based on the classification, outputting signals to control an I/O device, such that what content is displayed by the I/O depends, a least in part, on the classification. In some cases: (a) the first set of light sources includes a first light source and a second light source; and (b) the first light source emits a spectrum of light that is different than the spectrum of light emitted by the second light source. In some cases, the coherent light and incoherent light illuminate the surface at different times. In some cases, the first and second sets of light sources, taken together, illuminate the surface in a temporal sequence of illumination patterns. In some cases, direction and spectrum of illumination produced by the first set of light sources vary over time. In some cases: (a) the one or more computers include a first computer and a second computer; (b) at least the one or more cameras, the first and second sets of light sources, and the first computer are housed in a housing; (c) the first computer takes, an input, data from the one or more cameras, extracts parameter values from the data, and sends the parameter values to the second computer; and (d) the second computer takes the parameter values as input, and computes a classification of the surface. In some cases, the surface is transparent. In some cases, the surface is specular. In some cases: (a) the one or more cameras include a first camera and a second camera; (b) the first and second cameras capture images of the surface; and (c) the first camera has a spectral sensitivity that is different than the spectral sensitivity of the second camera. In some cases: (a) the first set of light sources includes a first light source and a second light source; (b) the first light source has a first emission spectrum and the second light source has a second emission spectrum; and (c) the first emission spectrum is different than the second emission spectrum. Each of the cases described above in this paragraph is an example of the method described in the first sentence of this paragraph, and is also an example of an embodiment of this invention that may be combined with other embodiments of this invention.

In another aspect, this invention is an apparatus comprising, in combination: (a) a first set of one or more incoherent light sources for illuminating a surface with incoherent light; (b) a second set of one or more coherent light sources for illuminating the surface with coherent light; (c) one or more cameras for capturing images of the surface while the surface is illuminated with the incoherent light and while the surface is illuminated with the coherent light; and (d) one or more machine-readable media with instructions encoded thereon for one or more computers (i) to take, as input, data indicative of or derived from the images, and (ii) to determine a classification of the surface, and based on the classification, to output signals to control an I/O device, such that what content is displayed by the I/O device depends, at least in part, on the classification. In some cases: (a) the first set of light sources includes a first light source and a second light source; (b) the first light source has a first emission spectrum and the second light source has a second emission spectrum; and (c) the first emission spectrum is different than the second emission spectrum. In some cases, an angle exists, such that: (a) a point in the surface is within the camera's field of view and is a vertex of an angle; (b) the angle is formed by two lines that diverge from the vertex and that intersect the first and second light sources, respectively; and (c) the angle is at least thirty degrees. In some cases, the instructions include instructions for the one or more computers to cause the first and second sets of light sources, taken together, to illuminate the surface in a temporal sequence of illumination patterns. In some cases, the instructions include instructions for the one or more computers to cause direction and spectrum of illumination produced by the first set of light sources to vary over time. Each of the cases described above in this paragraph is an example of the apparatus described in the first sentence of this paragraph, and is also an example of an embodiment of this invention that may be combined with other embodiments of this invention.

In another aspect, this invention is an apparatus comprising, in combination: (a) a first set of one or more incoherent light sources for illuminating a surface with incoherent light; (b) a second set of one or more coherent light sources for illuminating the surface with coherent light; (c) one or more cameras for capturing images of the surface while the surface is illuminated with the incoherent light and while the surface is illuminated with the coherent light; and (d) one or more computers programmed (i) to take, as input, data indicative of or derived from the images, and (ii) to determine a classification of the surface, and based on the classification, to output signals to control an I/O device, such that what content is displayed by the I/O device depends, at least in part, on the classification. In some cases: (a) the first set of light sources includes a first light source and a second light source; (b) the first light source has a first emission spectrum and the second light source has a second emission spectrum; and (c) the first emission spectrum is different than the second emission spectrum. In some cases, the one or more computers are programmed to cause direction and spectrum of illumination produced by the first set of light sources to vary over time. In some cases: (a) the one or more computers include a first computer and a second computer; (b) at least the one or more cameras, the first and second sets of light sources, and the first computer are housed in a housing; (c) the first computer is programmed to take, as input, data from the camera, to extract parameter values from the data, and to send the parameter values to the second computer; and (d) the second computer is programmed to take the parameter values as input, and to compute a classification of the surface. In some cases, the one or more cameras and the first and second sets of light sources are housed in a mobile communication device. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. A method comprising, in combination:
   (a) a first set of one or more light sources illuminating an external surface of an object with coherent light during a first time period;
   (b) a second set of one or more light sources illuminating the external surface with incoherent light during a second time period, such that the first time period and the second time period do not overlap;
   (c) one or more cameras capturing images of the external surface
      (i) during the first time period while the external surface is illuminated with the coherent light, and
      (ii) during the second time period while the external surface is illuminated with the incoherent light; and
   (d) one or more computers
      (i) taking, as input, data indicative of or derived from the images,
      (ii) determining a classification of the external surface, and
      (iii) based on the classification, outputting signals to control an input/output (I/O) device, such that what content is displayed by the I/O depends, a least in part, on the classification;
   wherein
      (1) features are embedded in a transparent layer, which layer is illuminated by the coherent light during the first time period and by the incoherent light during the second time period,
      (2) the features are invisible to an unaided human eye and have material properties that are different than the transparent layer, and
      (3) the content that is displayed by the I/O device depends on data encoded by the features.

2. The method of claim 1, wherein direction and spectrum of illumination produced by the first set of light sources vary over time.

3. The method of claim 1, wherein:
   (a) the one or more computers include a first computer and a second computer;
   (b) at least the one or more cameras, the first and second sets of light sources, and the first computer are housed in a housing;
   (c) the second computer is outside of the housing;
   (d) the first computer takes, as an input, data from the one or more cameras, extracts parameter values from the data, and outputs the parameter values for wireless transmission to the second computer; and
   (e) the second computer takes the parameter values as input, and computes a classification of the surface in real time.

4. The method of claim 1, wherein:
   (a) the one or more cameras include a first camera and a second camera;
   (b) the first and second cameras capture images of the surface; and
   (c) the first camera has a spectral sensitivity that is different than the spectral sensitivity of the second camera.

5. The method of claim 3, wherein the parameters values, which are extracted by the first computer and are wirelessly transmitted to the second computer, include average pixel intensity of a frame.

6. The method of claim 1, wherein the surface that is classified is specular) The method of claim 3, wherein the parameter values, which are extracted from the data and are wirelessly transmitted to the second computer, include number of valid feature points in a frame.

7. An apparatus comprising, in combination:
   (a) a first set of one or more coherent light sources for illuminating an external surface of an object with coherent light during a first time period;
   (b) a second set of one or more incoherent light sources for illuminating the external surface with incoherent light during a second time period, such that the first time period and the second time period do not overlap;
   (c) one or more cameras for capturing images of the external surface
      (i) during the first time period while the external surface is illuminated with the coherent light, and
      (ii) during the second time period while the external surface is illuminated with the incoherent light; and
   (d) one or more computers programmed
      (i) to take, as input, data indicative of or derived from the images, and
      (ii) to determine a classification of the external surface, and based on the classification, to output signals to control an input/output (I/O) device, such that what content is displayed by the I/O device depends, at least in part, on the classification;
   wherein
      (1) features are embedded in a transparent layer, which layer is illuminated by the coherent light during the first time period and by the incoherent light during the second time period,
      (2) the features are invisible to an unaided human eye and have material properties that are different than the transparent layer, and
      (3) the content that is displayed by the I/O device depends on data encoded by the features.

8. The apparatus of claim 7, wherein the one or more computers are programmed to cause direction and spectrum of illumination produced by the first set of light sources to vary over time.

9. The apparatus of claim 7, wherein:
   (a) the one or more computers include a first computer and a second computer;

(b) at least the one or more cameras, the first and second sets of light sources, and the first computer are housed in a housing;
(c) the second computer is outside of the housing;
(d) the first computer is programmed to extract parameter values from the images, and to output the parameter values for wireless transmission to the second computer; and
(e) the second computer is programmed to take the parameter values as input, and to compute a classification of the surface in real time.

10. The apparatus of claim 9, wherein the parameter values, which are extracted from the images by the first computer and are wirelessly transmitted to the second computer, include average pixel intensity of a frame.

11. The apparatus of claim 9, wherein the parameter values, which are extracted from the images by the first computer and are wirelessly transmitted to the second computer, include number of valid feature points in a frame.

12. The apparatus of claim 9, wherein, for a given frame, the parameter values, which are extracted from the images by the first computer and are wirelessly transmitted to the second computer:
(a) are represented by four bytes of wirelessly transmitted data; and
(b) include (i) average pixel intensity of the given frame, (ii) darkest pixel of the given frame, (iii) brightest pixel of the given frame, and (iv) number of valid feature points in the given frame.

* * * * *